United States Patent [19]

Matkovich et al.

[11] Patent Number: 5,070,899
[45] Date of Patent: Dec. 10, 1991

[54] CHECK VALVE

[75] Inventors: Vlado I. Matkovich, Glen Cove, N.Y.; Sidney Krakauer, Highland Beach, Fla.

[73] Assignee: Pall Corporation, Glen Cove, N.Y.

[21] Appl. No.: 357,676

[22] Filed: May 26, 1989

Related U.S. Application Data

[63] Continuation of Ser. No. 925,918, Nov. 3, 1986, abandoned.

[51] Int. Cl.⁵ .................... F16K 17/00; A61M 5/38
[52] U.S. Cl. .................................. 137/455; 137/177; 137/251.1; 210/335; 604/126; 604/251
[58] Field of Search ............ 137/154, 177, 198, 251.1, 137/455; 604/126, 251, 252, 253, 254, 255; 210/335

[56] References Cited

U.S. PATENT DOCUMENTS

| | | | |
|---|---|---|---|
| 1,846,307 | 2/1932 | Bush | 137/177 X |
| 1,973,259 | 9/1934 | Kiefer | 137/177 |
| 2,719,537 | 10/1955 | Gildersleeve | 137/251.1 |
| 2,834,366 | 5/1958 | Bond | 137/251.1 |
| 3,111,959 | 11/1963 | Allen et al. | 137/251.1 |
| 3,523,408 | 8/1970 | Rosenberg . | |
| 3,650,093 | 3/1972 | Rosenberg . | |
| 3,882,026 | 5/1975 | McPhee . | |
| 4,013,072 | 3/1977 | Jess | 137/177 X |
| 4,030,495 | 6/1977 | Virag . | |
| 4,116,646 | 9/1978 | Edwards | 604/252 X |
| 4,136,693 | 1/1979 | Dyke | 137/177 X |
| 4,177,149 | 12/1979 | Rosenberg . | |
| 4,190,426 | 2/1980 | Ruschke . | |
| 4,200,095 | 4/1980 | Reti . | |
| 4,340,479 | 7/1982 | Pall . | |
| 4,352,364 | 10/1982 | Orsino et al. . | |
| 4,412,916 | 11/1983 | Kell . | |
| 4,503,565 | 3/1985 | Lippitt et al. | 128/201.28 X |

FOREIGN PATENT DOCUMENTS 45-24752 8/1970 Japan ................. 137/251.1

Primary Examiner—Gerald A. Michalsky
Attorney, Agent, or Firm—Leydig, Voit & Mayer

[57] ABSTRACT

The disclosure describes a check valve comprising a structure for channeling a flow of a first fluid and first and second porous elements for permitting flow of the first fluid and substantially preventing flow of a second fluid. The first and second porous elements extend across the channeling structure, engaging and sealing against the channeling structure to define a pocket between the first and second porous elements. The pocket contains the second fluid.

1 Claim, 1 Drawing Sheet

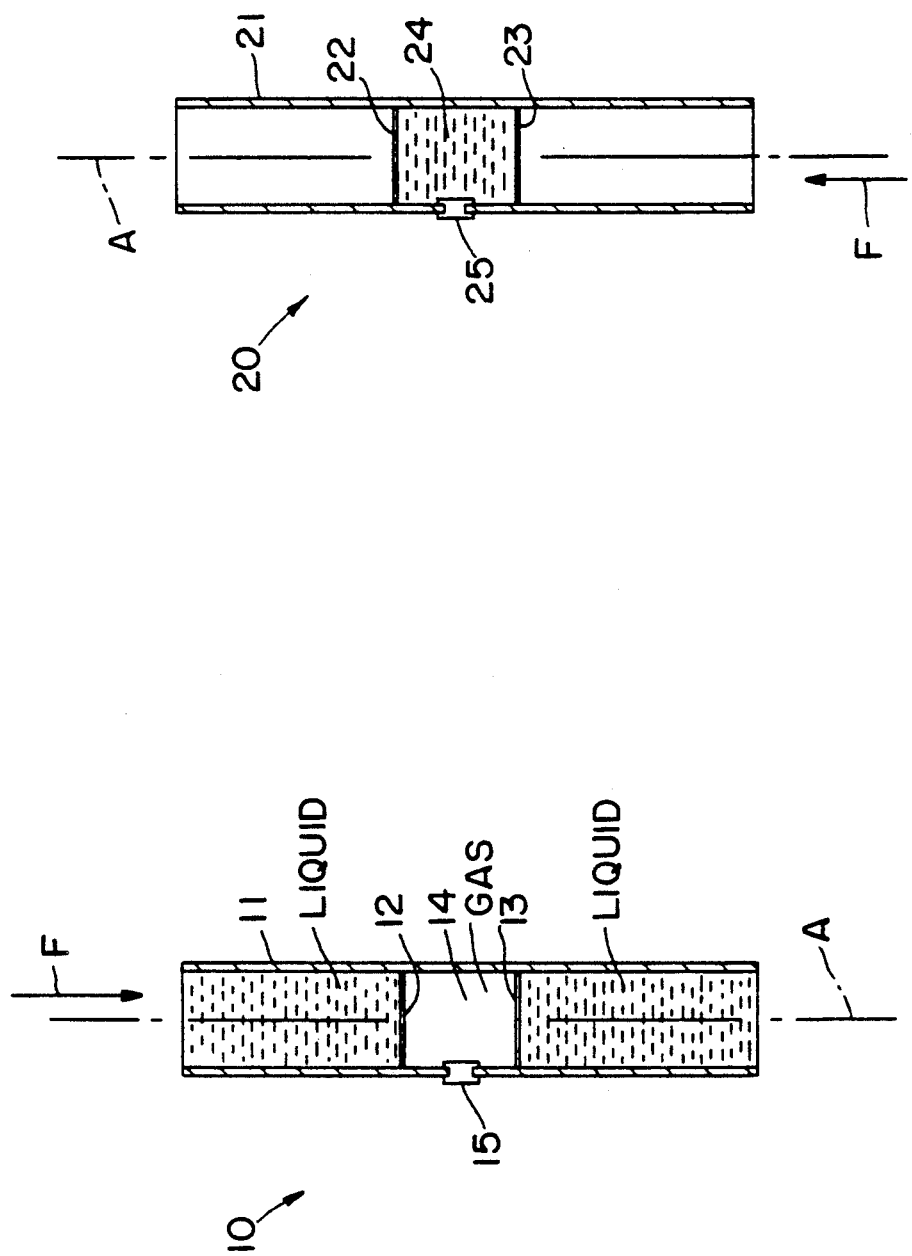

CHECK VALVE

This application is a continuation of application Ser. No. 06/925,918, filed Nov. 3, 1986, now abandoned.

TECHNICAL FIELD

The present invention is directed to valves, particularly check valves or valves that permit flow in one direction and prevent or substantially prevent flow in the opposite direction.

BACKGROUND OF THE INVENTION

It has long been recognized that, in certain systems for the handling of fluids, there is a need for a valve in a flow line which allows a fluid to flow in one direction but prevents the fluid from flowing in the opposite direction. Such valves are generally referred to as check valves.

One form of check valve is the ball-and-socket check valve. The socket typically has an opening. The ball, which is larger than the opening, is fitted to the socket adjacent the opening and in contact with the fluid. When the fluid forces the ball away from the socket, the fluid flows in one direction through the opening. However, when the fluid forces the ball against the socket, the ball blocks the opening and substantially prevents the fluid from flowing in the opposite direction through the opening.

Unfortunately, many check valves do not completely prevent fluid from flowing in the opposite direction. For example, when the ball of the ball-and-socket check valve is forced against the socket, it may not perfectly seal the opening, permitting a significant flow of fluid in the opposite direction. This flow in the opposite direction is called backflow. Thus, these check valves are suitable only when a slight or moderate amount of backflow is acceptable.

There is frequently a need for a check valve that substantially eliminates backflow. For example, in the medical arts, patients frequently require intravenous administration of two therapeutic solutions simultaneously. Each solution is contained in a separate bag or bottle which is hung from a stand and connected to the patient by a tube. The tubes from the bags are typically joined at a Y connector and then channeled to the patient via a common tube terminating in a single needle.

In order to accurately administer these therapeutic solutions to the patient, it is important that the solutions only flow from their respective bags to the patient. However, in certain circumstances, for example, when one bag is hung higher than the other and the common tube is clamped shut, the solution in one bag may flow through the Y connector into the other bag. A check valve which effectively eliminates any backflow through the tubes leading from the bags would be extremely beneficial.

DISCLOSURE OF THE INVENTION

The present invention provides a check valve comprising structure for channeling the flow of a first fluid and first and second porous elements, each permitting flow of the first fluid and substantially preventing flow of a second fluid. The first and second porous elements extend across the channeling structure, engaging and sealing against the channeling structure and defining a pocket between the elements. The pocket contains the second fluid.

Check valves embodying the present invention operate on the principal that a layer of one fluid may be trapped between two porous elements while another fluid may be passed in one direction, but not the opposite direction, through the layer of trapped fluid. For example, the present invention provides a check valve wherein a gas is contained in the pocket between the first and second porous elements. The check valve is oriented, for example, generally vertically, such that a fluid can flow downward through the channeling structure, through one porous element, and into the pocket. The liquid then passes downwardly through the gas in the pocket and through the other porous element and then continues to flow downwardly along the channeling structure. The liquid is prevented from flowing in the reverse direction, i.e., upwardly, through the check valve because the liquid, being more dense than the gas, cannot flow upwardly through the trapped layer of gas between the porous elements.

As another example, the present invention provides a check valve wherein a liquid is contained in the pocket between the first and second porous elements. The check valve is oriented, for example, again generally vertically, such that a gas can flow upwardly through the channeling structure, through one porous element, and into the pocket. The gas then moves upwardly through the liquid and through the other porous element before continuing its upward flow through the channeling structure. The gas is prevented from flowing in the opposite direction, i.e., downwardly through the channeling structure, by the layer of liquid trapped between the first and second porous elements.

BRIEF DESCRIPTION OF THE DRAWINGS

In the accompanying drawings:

FIG. 1 is a sectional elevation view of a first embodiment of a check valve in accordance with the present invention, and FIG. 2 is a sectional elevation view of a second embodiment of a check valve in accordance with the present invention.

BEST MODE FOR CARRYING OUT THE INVENTION

A check valve constructed and operated according to the present invention may be used to control the flow of a variety of fluids, including many liquids and gases. For example, the first exemplary check valve 10, shown in FIG. 1, may be used to control the flow of a liquid while the second exemplary check valve 20, shown in FIG. 2, may be used to control the flow of a gas.

The first exemplary check valve 10 generally comprises a structure 11 for channeling the flow of a first liquid and first and second porous elements 12, 13 which extend across the channeling structure 11, defining a pocket 14 which contains a second fluid. The second fluid is less dense than the first liquid and preferably comprises a gas such as air. Alternatively, the second fluid may comprise a second liquid which is not only less dense than but also immiscible in the first liquid.

The channeling structure 11 may include a small opening between the first and second porous elements 12, 13 which is sealed by a rubber septum 15 or other seal This opening-and-seal arrangement may be used to initially introduce or to replenish the second fluid in the pocket 14. Further, the channeling structure 11 may be configured as a cylindrical conduit such as a pipe or tube, as illustrated, or in any other suitable geometry. It may be rigid or flexible and may be fabricated from any sufficiently impervious material, including a thermoplastic material.

The first and second porous elements 12, 13 extend across the channeling structure 11 preferably in a direction generally perpendicular to the longitudinal axis A of the channeling structure 11, i.e., generally perpendicular to the direction of flow F. The edge of each porous element 12, 13 is attached to the channeling structure 11 by an adhesive or in any other manner suitable for joining the porous element 12, 13 to the channeling structure 11 and effecting a seal between them.

The first and second porous elements 12, 13 may have any suitable porous structure, including a microporous structure. For example, the porous elements 12, 13 may have an absolute pore rating in the range from about 0.2 micrometer to about 5.0 micrometers and a bubble point for water in the range from about 40 psi to about 7 psi, respectively. Further, the porous elements 12, 13 may be fashioned from any suitable porous material, including a fibrous or membranous material. For example, the porous elements 12, 13 preferably comprise microporous membranes.

For the first exemplary check valve 10, the first and second porous elements 12, 13 are preferably liquiphilic with respect to the first liquid, i.e., wettable by the first liquid in that the first liquid readily flows along and through each porous element 12, 13 filling the pores and passageways of the element 12, 13. For example, if the first exemplary check valve 10 is used to control the flow of the first liquid comprising water or a water-based solution, the first and second porous elements 12, 13 may each comprise a porous membrane which is hydrophilic, i.e., readily wettable by water. Such hydrophilic porous membranes may be fashioned from nylon or cellulose esters, such as cellulose acetate.

If the second fluid is a second liquid, the first and second porous elements 12, 13 may also be liquiphobic with respect to the second liquid, i.e., resistant to wetting by the second liquid in that the second liquid does not readily flow through the pores and passageways of the porous element 12, 13. For example, if the first liquid comprises water and the second liquid comprises an oil which is less dense than and immiscible in water, the first and second porous elements 12, 13 may each be oleophobic, i.e., resistant to wetting by oil, as well as hydrophilic.

In the preferred mode of operation of the first exemplary check valve 10, the first and second porous elements 12, 13 may initially be wetted by the first liquid. For example, the check valve may be oriented vertically with the second porous element 13 above the first porous element 12. The first liquid may then be directed down through the channeling structure 11 until it contacts and wets the second porous element 13. The check valve 10 is then inverted and the first liquid is directed down through the channeling structure 11 until it contacts and wets the first porous element 12.

Once the first and second porous elements 12, 13 have been wetted, the second fluid, e.g., a gas or a second immiscible liquid, may be introduced into the pocket 14 through the seal 15. For example, a hollow needle attached to a syringe (not shown) filled with the second fluid may be forced through the seal 15 into the pocket 14. The second fluid may then be forced through the needle into the pocket 14 by the syringe. A second hollow needle inserted into the pocket 14 through the seal 15 may serve as a vent from removing any air in the pocket 14 when the second fluid is forced into the pocket 14. After the pocket 14 is filled with the second fluid, both needles are withdrawn, the seal 15 closing and sealing the pocket 14 as the needles are withdrawn. The second fluid is then contained within the pocket 14 by the wetted porous elements 12, 13.

Alternatively, if the second fluid is air, the pocket 14 may be filled with air without initially wetting the first and second porous elements 12, 13. Before the porous elements 12, 13 have been wetted, air freely passes through them into the pocket 14. With the pocket 14 thus filled with air, the check valve 10 may be oriented vertically with the first porous element 12 over the second porous element 13, as shown in FIG. 1. The first liquid is then directed downwardly through the channeling structure 11 until it contacts and wets the first porous element 12. The liquid then passes through the first porous element 12 and the pocket 14 and then contacts and wets the second porous element 13. If the rate of flow of the first liquid through the pocket 14 is not too great, e.g., if the first liquid drips from the first porous element 12 onto the second porous element 13, the first liquid will not significantly displace the air in the pocket 14 before the second porous element 13 is wetted, and the air will remain contained in the pocket 14 between the wetted elements 12, 13.

A flow F of the first liquid is then directed generally downwardly through the check valve 10, while the second fluid remains trapped in the pocket 14. If the second fluid is a gas, it is prevented from flowing through the wetted first and second porous elements 12, 13 because the pores and passageways of the elements 12, 13 are filled with the first liquid. If the second fluid is an immiscible second liquid, it too is prevented from flowing through the wetted first and second porous elements 12, 13. Not only are the pores and passageways of the elements 12, 13 filled with the first liquid, but, in the preferred embodiment, the first and second porous elements 12, 13 are liquiphobic with respect to the second liquid and therefore resist any flow of the second liquid from the pocket 14. As long as the differential pressure across the porous elements 12, 13 is insufficient to force the second fluid through the first liquid-filled pores, the second fluid is contained in the pocket 14. Thus, the porous elements 12, 13 permit the first liquid to flow downwardly through the check valve 10 but prevent the second fluid from escaping from the pocket 14.

The flow rate of the first liquid depends on many factors, including the porosity of the elements 12, 13 as well as the differential pressure across the check valve 10. Larger pores may require smaller differential pressures because the second fluid may be more easily blown through the larger pores.

In accordance with one aspect of the invention, while the first liquid may flow in one direction, i.e., downwardly, through the first exemplary check valve 10, backflow, i.e., flow of the liquid in the opposite direction, is prevented. Whenever a reverse pressure sufficient to direct a flow of fluid upwardly through the check valve 10 is applied, the first liquid may pass upwardly through the second porous element 13 but is prevented from passing through the pocket 14 by the second fluid. If the second fluid is a gas or a second liquid which is less dense than and immiscible in the first liquid, a layer of the second fluid will remain between the first porous element 12 and the first liquid, preventing the first liquid from flowing upwardly through the pocket 14 and the first porous element 12. Again, as long as the reverse pressure is not sufficient to force the second fluid through the first liquid-filled pores of the first porous element 12, the second fluid will be retained in the pocket 14 and the upward flow of the first liquid will be checked by the layer of second fluid.

To prevent backflow of the first liquid, it is preferable to space the first and second porous elements 12, 13 sufficiently far apart to prevent the first liquid from spanning the pocket 14 between the elements 12, 13 even if the check valve 10 is tilted slightly. For example, if the distance between the first and second porous elements 12, 13 is slightly greater than the diameter of the channeling structure 11, the first liquid will not span the pocket 14 between the elements 12, 13 even if the pocket 14 is half filled with the first liquid and the check valve 10 is tilted as much as 45 degrees from the vertical.

The first exemplary check valve 10 may be used in a wide variety of applications. For example, it may be used as a drip chamber of an administration set for administering liquids to a patient. One particularly significant advantage of using the first exemplary check valve 10 as a drip chamber is that it will prevent a fluid line to the patient from running dry. Once all of the liquid to be administered to the patient has passed through the first porous element 12, flow to the patient will cease and the portion of the fluid line to the patient below the second porous element 13 will retain the liquid being administered.

As shown in FIG. 2, the second exemplary check valve 20 also comprises a structure 21 for channeling the flow of a first fluid and first and second porous elements 22, 23 which extend across the channeling structure 21, similarly defining a pocket 24 containing a second fluid and sealed by a seal 25. For the second exemplary check valve 20, the first fluid may comprise a gas or a first liquid while the second fluid is more dense than the first fluid and preferably comprises a second liquid which is also immiscible in the first liquid.

The channeling structure 21 of the second exemplary check valve 20 may be identical to that of the first exemplary check valve 10. The first and second porous elements 22, 23 may similarly extend across the channeling structure 21 generally perpendicularly to the longitudinal axis A of the channeling structure 21 and the direction of flow F, and they may be similarly sealed to the channeling structure 21. Further, the first and second porous elements 22, 23 may similarly be fashioned from any suitable porous material, preferably microporous membranes, and are preferably liquiphilic with respect to the first liquid, if the first fluid is a first liquid, and liquiphobic with respect to the second liquid. For example, if the first fluid comprises air and the second liquid comprises water, the first and second porous elements 22, 23 may each comprise a porous membrane which is hydrophobic, i.e., resists wetting by water. Such porous, hydrophobic membranes may be fashioned from TEFLON, polyvinylidene difluoride, or polypropylene.

In the preferred mode of operation of the second exemplary check valve 20, the second liquid is initially introduced into the pocket 24 through the seal 25 in a manner analogous to that of the first exemplary check valve 10. A flow F of the first fluid is then directed generally upwardly through the check valve 20, while the second liquid remains trapped in the pocket 24. Upon encountering the second porous element 23, the first fluid passes through the second porous element 23 into the pocket 24 containing the second liquid. Since the first fluid is less dense than the second liquid, it moves upwardly through the pocket 24. Upon encountering the first porous element 22, the first fluid passes through the first porous element 22 and continues its upward flow along the channeling structure 21. Because the first and second porous elements 22, 23 are liquiphobic with respect to the second liquid, the second liquid is prevented from flowing through the porous elements 22, 23 and remains contained in the pocket 24. As long as the differential pressure across the porous elements 22, 23 is insufficient to force the second liquid through the porous elements 22, 23, the liquid is retained in the pocket 24. Thus, the porous elements 22, 23 permit the first fluid to flow through the check valve 20 but prevent the second liquid from flowing from the pocket 24.

In accordance with another aspect of the invention, backflow, i.e., flow of the first fluid in the opposite direction, is prevented. Whenever a reverse pressure sufficient to direct fluid flow downwardly through the check valve 20 is applied, the first fluid may pass downwardly through the first porous element 22 into the pocket 24. However, since the first fluid is less dense than the liquid, and, if the first fluid comprises a first liquid, the first liquid is preferably immiscible in the second liquid, a layer of the second liquid will remain between the second porous element 23 and the first fluid, preventing the first fluid from flowing downwardly through the check valve 20. Again, as long as the reverse pressure is insufficient to force the second liquid through the second porous element 22, the second liquid will be retained in the pocket 24 and the downward flow of the first fluid will be checked.

While the invention has been described in terms of two exemplary embodiments, it is not limited to those embodiments. Alternative embodiments and modifications which would still be encompassed by the invention may be made by those skilled in the art, particularly in light of the foregoing teachings. Therefore, the following claims are intended to cover any alternative embodiments, modifications, or equivalents which may be included within the spirit and scope of the invention.

What is claimed is:

1. A check valve comprising a conduit having a longitudinal axis and first and second porous membranes extending across the conduit generally perpendicularly to the longitudinal axis, said conduit further having an opening between the first and second porous membranes and a septum which seals the opening and said first and second porous membranes sealingly engaging the conduit and said first porous membrane being spaced from said second porous membrane by a distance which is at lest substantially equal to the diameter of the conduit and said first and second porous membranes having absolute pore ratings in the range from about 0.2 micrometer to about 5.0 micrometers.

* * * * *